(12) United States Patent
Hacker et al.

(10) Patent No.: US 7,628,756 B2
(45) Date of Patent: Dec. 8, 2009

(54) EXTRACORPOREAL EMBOLI DETECTOR

(75) Inventors: Thomas G. Hacker, Anaheim, CA (US); Brent William Allen, Rancho Santa Margarita, CA (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 503 days.

(21) Appl. No.: 11/367,880

(22) Filed: Mar. 4, 2006

(65) Prior Publication Data

US 2006/0241485 A1    Oct. 26, 2006

Related U.S. Application Data

(60) Provisional application No. 60/659,260, filed on Mar. 7, 2005.

(51) Int. Cl.
*A61B 8/14* (2006.01)

(52) U.S. Cl. ........................ 600/467; 600/459

(58) Field of Classification Search ................ 600/459
See application file for complete search history.

(56) References Cited

U.S. PATENT DOCUMENTS

| | | | |
|---|---|---|---|
| 3,515,128 A * | 6/1970 | Mcevoy | 600/566 |
| 4,989,606 A | 2/1991 | Gehrich et al. | |
| 5,842,994 A * | 12/1998 | TenHoff et al. | 600/466 |
| 6,208,880 B1 | 3/2001 | Bentsen et al. | |
| 6,231,564 B1 * | 5/2001 | Gambale | 604/528 |
| 2001/0000185 A1 * | 4/2001 | Keller et al. | 604/6.02 |
| 2002/0062134 A1 * | 5/2002 | Barbut et al. | 606/200 |
| 2003/0023168 A1 * | 1/2003 | Benjamin | 600/459 |
| 2003/0055309 A1 * | 3/2003 | Kaushansky et al. | 600/18 |
| 2003/0109777 A1 * | 6/2003 | Kloepfer et al. | 600/367 |
| 2003/0208103 A1 * | 11/2003 | Sonnenschein et al. | 600/117 |
| 2004/0122323 A1 * | 6/2004 | Vortman et al. | 600/459 |

* cited by examiner

*Primary Examiner*—Long V Le
*Assistant Examiner*—Hien Nguyen
(74) *Attorney, Agent, or Firm*—Gael Diane Tisack, Esq.; MacMillian Sobanski & Todd, LLC

(57) ABSTRACT

An emboli detector device receives a blood flow in a perfusion circuit. The connector-like device has a rigid plastic smooth body hermetically sealed from the blood. There is a calculated thin, but rigid window formed as part of the flow-through tubing wall to allow ultrasonic waves to interrogate the flowing blood. A dampening material is included in the ultrasound path to adjust the acoustic levels to an applicable range to monitor emboli. The device incorporates a mechanism to securely hold the transducer during operation and a sensing system for automatically informing a control system of which one of several standard perfusion circuit tubing diameters is being used. The ultrasound echoes detected by the transducer are provided to a controller which detects the emboli and provides a detection signal to warn the surgeon or other operating room personnel of the embolic event.

16 Claims, 5 Drawing Sheets

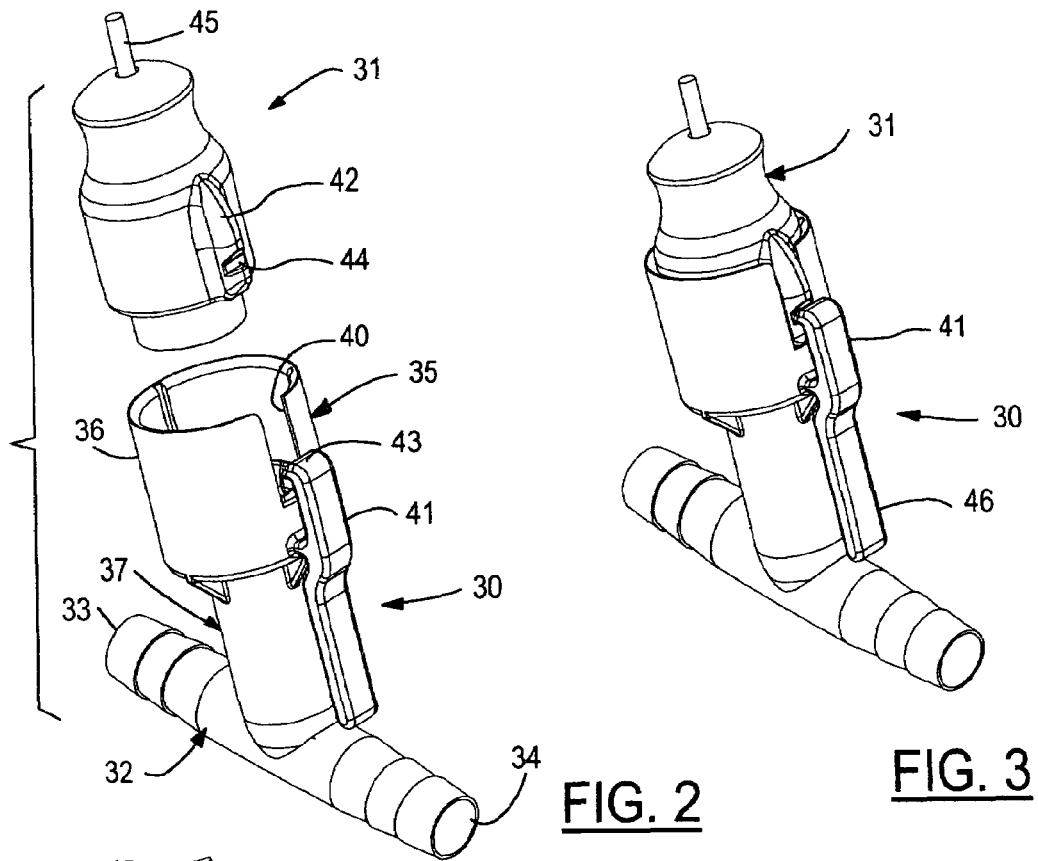
FIG. 2
FIG. 3
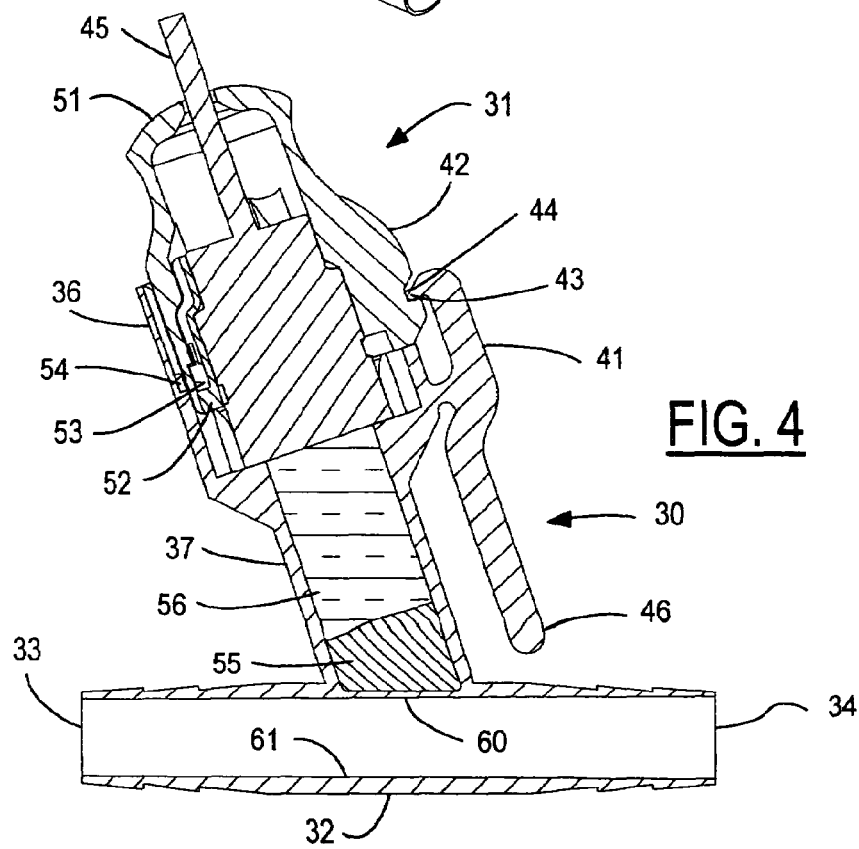
FIG. 4

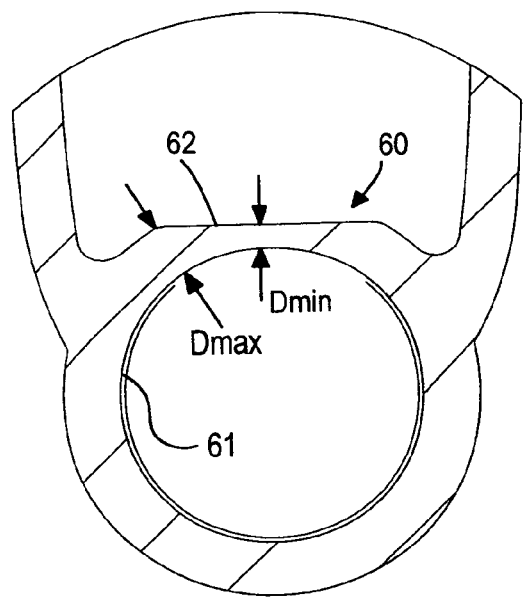
FIG. 5
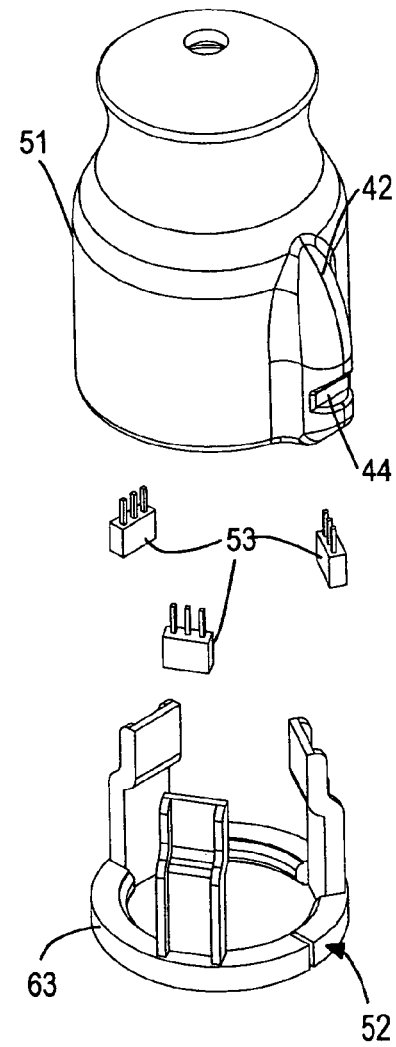
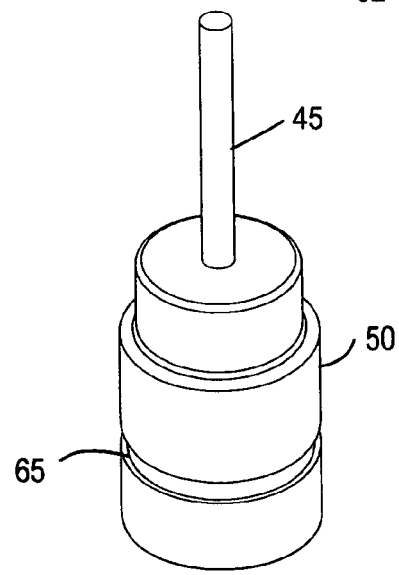
FIG. 6

EXTRACORPOREAL EMBOLI DETECTOR

CROSS REFERENCE TO RELATED APPLICATIONS

This application claims priority to co-pending U.S. provisional application Ser. No. 60/659,260, filed Mar. 7, 2005.

STATEMENT REGARDING FEDERALLY SPONSORED RESEARCH

Not Applicable.

BACKGROUND OF THE INVENTION

The present invention relates in general to blood monitoring during cardiovascular surgery, and, more specifically, to a device for detecting emboli in the extracorporeal blood during on pump coronary bypass surgery.

When bypass is used during cardiac surgery, steps must be taken in order to avoid neurological injury. Neurological risks include reduced cognitive abilities and stroke. Emboli (i.e., air bubbles or particulates) entering the blood circuit from the heart, aortic walls or other areas can cause these problems if allowed to enter the brain during surgery. It is desirable to have a method of detecting the emboli in the cardiac perfusion circuit before it reaches the brain so that surgical technique adjustments can be made to reduce or prevent the emboli.

Transcranial Doppler systems are known for monitoring emboli entering the brain during surgery, but these systems do not detect emboli until after they have reached the brain. A system that detects the emboli earlier in the perfusion circuit would be desirable because preventive measures can then be put in place prior to the emboli reaching the brain. Besides localizing the site where emboli are entering the system (e.g., in the pump and/or at the surgical field), detection prior to entry into the patient may allow rerouting or deactivation of a blood circuit to prevent the detected emboli from reaching the brain.

SUMMARY OF THE INVENTION

The present invention is a device used to couple an ultrasonic transducer at a fixed prescribed distance from blood flowing through an extracorporeal fluid circuit in order to detect passing emboli without affecting the blood flow. A connector-like device is disclosed wherein the blood can flow through the device in a manner similar to flowing through the circuit tubing. The connector-like device has a rigid plastic smooth body hermetically sealing blood from the environment. There is a calculated thin, but rigid window formed as part of the flow-through tubing wall to allow ultrasonic waves to interrogate the flowing blood. A dampening material is included in the ultrasound path to adjust the acoustic levels to an applicable range to monitor emboli. The connector like device can be preinstalled as a part of a complete extracorporeal tubing circuit or installed into a preexisting circuit using sterile techniques prior to being coupled to a patient. The device incorporates a mechanism to securely hold the transducer during operation and a sensing system for automatically informing a control system of which one of several standard perfusion circuit tubing diameters is being used. The ultrasound echoes detected by the transducer are provided to a controller which detects the emboli and provides a detection signal to warn the surgeon or other operating room personnel of the embolic event.

BRIEF DESCRIPTION OF THE DRAWINGS

FIG. 2 is an exploded perspective view of the detector.
FIG. 3 is a perspective view of the assembled device.
FIG. 4 is a vertical cross-section of the device of FIG. 3.
FIG. 5 is a transverse cross-section through the window and flow passageway.
FIG. 6 is an exploded view of the transducer element.

DETAILED DESCRIPTION OF PREFERRED EMBODIMENTS

Figure 1:
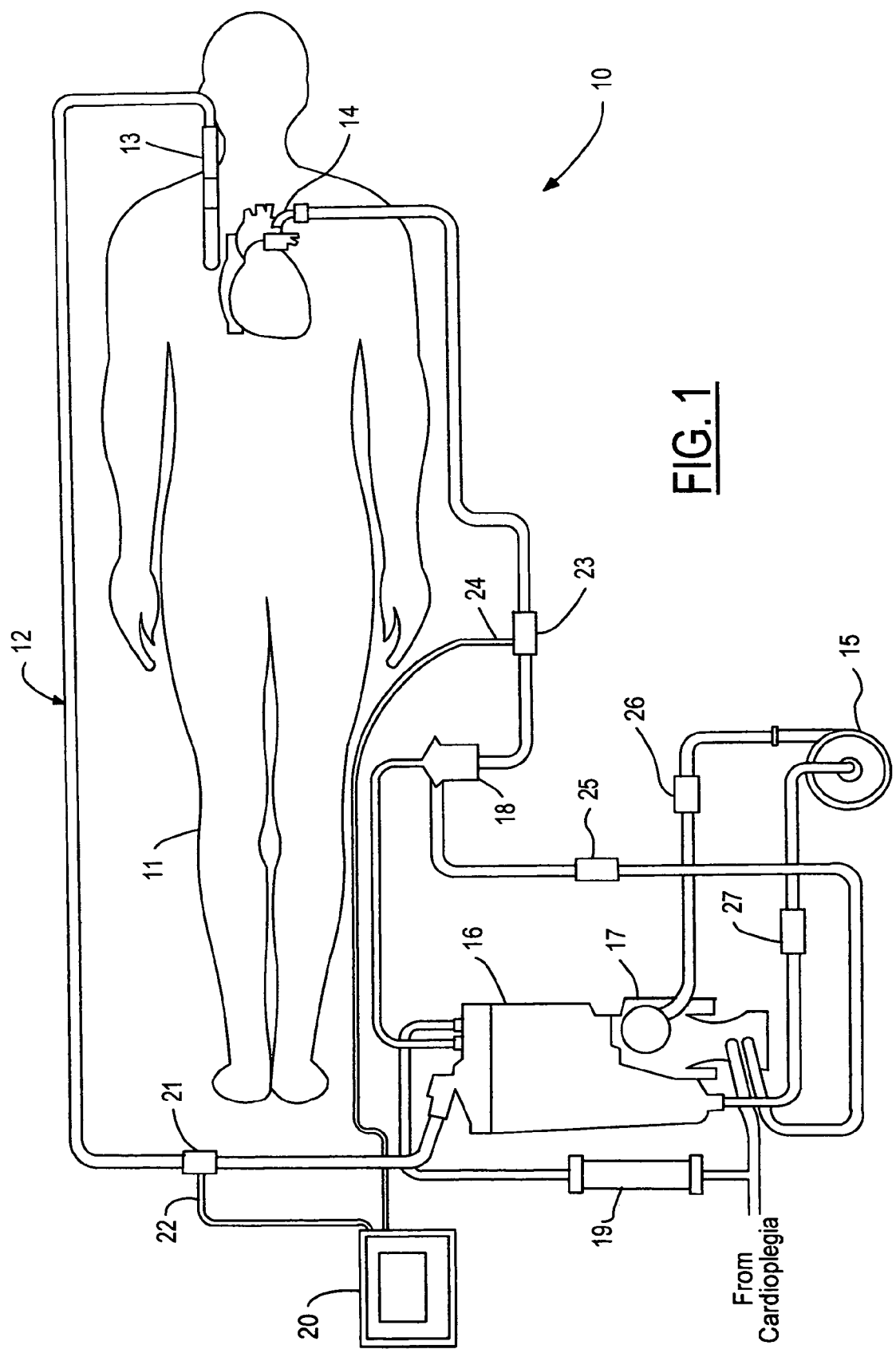
FIG. 1 is a schematic diagram showing a perfusion circuit and various potential locations for the extracorporeal emboli detector of the present invention.

Referring to FIG. 1, a perfusion system 10 is shown connected to a patient 11. Circuit tubing 12 circulates blood obtained at a venous catheter 13 and returned to the patient by an arterial cannula 14. Blood flow is created by a pump 15 using blood from a venous reservoir 16. A conventional oxygenator 17 provides oxygenated blood to an arterial filter 18, and a hemoconcentrator recirculates blood and can be used to introduce cardioplegia in a conventional manner.

An emboli controller/monitor 20 operates in conjunction with the detection apparatus of the present invention to provide monitoring of emboli in the extracorporeal blood circuit. It may be desirable to monitor blood flow for emboli at various locations in the perfusion circuit to maximize the ability to localize sites where emboli are entering the blood flow and to maximize the ability to isolate blood volumes that contain emboli. A first detector 21 is coupled in the circuit tubing between catheter 13 and reservoir 16. Electrical wiring 22 is connected between detector 21 and controller 20 to conduct signals associated with ultrasonic sensing and with special detection signals for identifying the size of circuit tubing as explained below. A detector 23 located between filter 18 and cannula 14 is connected to controller/monitor 20 by wiring 24. Additional potential locations for extracorporeal emboli detectors are shown at 25, 26, and 27.

The present invention employs ultrasonic interrogation of blood flowing through a tube in order to detect emboli. Due to the sterile nature of the perfusion process, tubing which contacts the blood is typically disposed of after one use. Although a dedicated ultrasonic testing unit for conveying blood to an ultrasonic sensor could be employed, the present invention reduces cost and complexity by providing an inexpensive disposable unit for connecting to the circuit tubing of the perfusion circuit and for receiving a conventional ultrasonic transducer element in a particular manner adapted to be able to sense emboli flowing in the blood. A first embodiment of the invention is shown in FIG. 2 wherein a disposable body member receives a reusable transducer member 31. Body member 30 includes a cylindrical flow passage 32 having an inlet 33 and an outlet 34. Passage 32 has the same internal diameter throughout as the perfusion circuit tubing and is adapted to be connected serially therewith. Body member 30 also includes a barrel piece 35 having an upper transducer mounting section 36 and a lower sound coupling section 37. Barrel piece 35 has a key slot 40 aligned with a release lever 41. Transducer member 31 has a keyed feature 42 that is received in key slot 40 as transducer member 31 is seated within upper transducer mounting section 36. A catch 43 on lever 41 mates with a groove 44 when transducer member 31 is completely seated within barrel piece 30. A wire cable 45 interconnects a transducer element with the controller and also carries a signal that identifies the size of flow passage 32 as will be described below.

FIG. 3 shows transducer member 31 fully seated within body member 30. By pressing on a remote end 46 of lever 41, catch 43 can be removed from groove 44 so that the transducer member 31 can be disassembled after use.

As shown in the cross section of FIG. 4, transducer member 31 includes an ultrasonic transducer element 50 and an adapter 51 for interfacing a conventional transducer element to the structures of the present invention. A frame 52 is disposed between transducer element 50 and adapter 51 for retaining a magnetic sensor 53, which may be comprised of a hall sensor. A magnet 54 is fixedly mounted to upper transducer mounting section 36 so that it is in close proximity to sensor 53 when transducer member 31 is properly seated.

In order to properly couple acoustic waves between transducer element 50 and blood to be interrogated for emboli, an inner chamber within lower sound coupling section 37 contains an acoustic dampening material 55 and an ultrasonic coupling gel 56. The bottom edge of lower sound coupling section 37 is bounded by an acoustic window 60. Acoustic dampening material 55 fills a first space at the lower end of section 37 of sufficient thickness and dampening coefficient to eliminate background noise from the received signal picked up by transducer element 50. Acoustic dampening material 55 may, for example, comprise a commercially available UV "cure-in-place" urethane acrylate A60 durometer gasket material.

Ultrasonic coupling gel 56 fills a second space between the first space and the transducer mounting section for insuring good acoustic coupling to and from transducer 50. Flow passage 32 includes a containment wall 61, which is preferably cylindrical in shape throughout for providing uninterrupted blood flow through the device. Containment wall 61 forms a bottom surface of acoustic window 60 so that the bottom surface is substantially cylindrically shaped. Window 60 has a substantially flat upper surface 62 that contacts dampening material 55. As shown in FIG. 5, acoustic window 60 has a variable thickness with a minimal thickness $D_{min}$ and a maximum thickness $D_{max}$. Preferably, the minimum thickness is greater than about 0.025 inches and is preferably in a range from about 0.025 inches to about 0.030 inches. Acoustic window 60 must be sufficiently thin to transmit sufficient acoustic signal therethrough. A minimum thickness in the range specified provides acceptable performance when the body member is formed of a thermoplastic chosen from any biocompatible material currently used in perfusion applications. Preferably, the body member is integrally molded as one piece for simple, disposable use and for ease of manufacturing.

FIG. 6 is an exploded view of the transducer member showing conventional ultrasonic transducer element 50, which is received by frame 52 having a ring portion 63 and clip members 64. Frame 52 receives transducer element 50 such that ring 63 may be captured in a groove 65 on the exterior of transducer element 50. Magnetic detectors 53 are respectively retained by clips 64 and are coupled via cable 45 to the controller by additional wiring (not shown). Frame 52 is keyed for insertion into adapter 51 in a single orientation so that each magnetic sensor is disposed at a predetermined position relative to keyed feature 42. Frame 52 may be retained within adapter 51 in the predetermined orientation by press-fitting, gluing, sonic welding, or any other known means of attachment.

Figure 7:
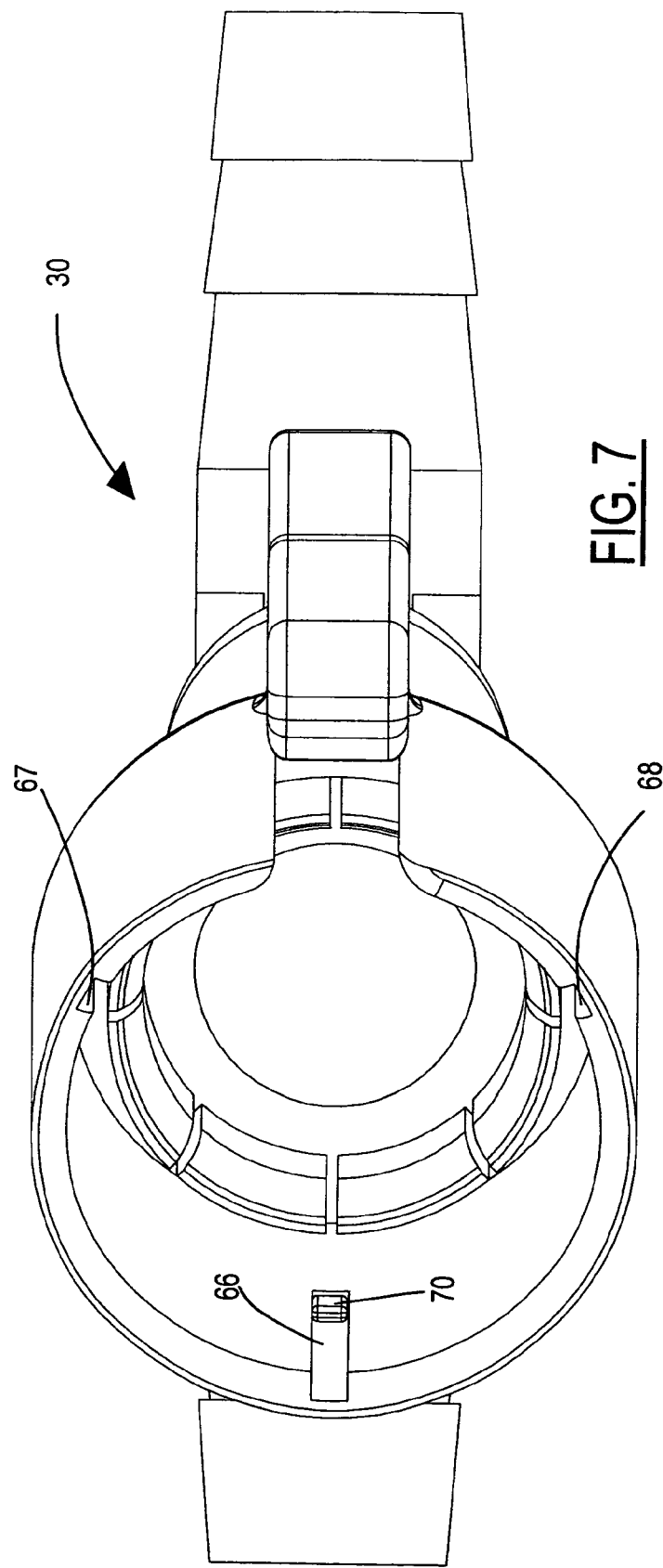
FIG. 7 is a top view of the body member.

FIG. 7 shows a top view of body member 30 showing the interior of upper transducer mounting section 36. Three longitudinal slots 66, 67, and 68 are provided, which are coincident with a respective clip 64 of the transducer member when it is inserted according to the matching key. Perfusion circuits typically are made up using one of three standard tubing sizes depending upon the size and/or sex of the patient. Correspondingly, the body member is manufactured according to one of the three standard sizes so that flow passage 32 provides a matching diameter. Depending upon which diameter is present for any particular unit, a small magnet is glued or otherwise attached into one of the respective slots 66-68 in order to identify the flow passage diameter. As shown in FIG. 7, a magnet 70 is provided in slot 66 for indicating one of the three possible diameters. When the transducer member is attached to any particular body member, the corresponding one of the magnetic sensors determines which of slots 66-68 contains a magnet and thereby infers the tubing diameter. This information is transmitted to the emboli controller/monitor in order to adapt the ultrasonic detection algorithm to the diameter of blood flow.

Figure 8:
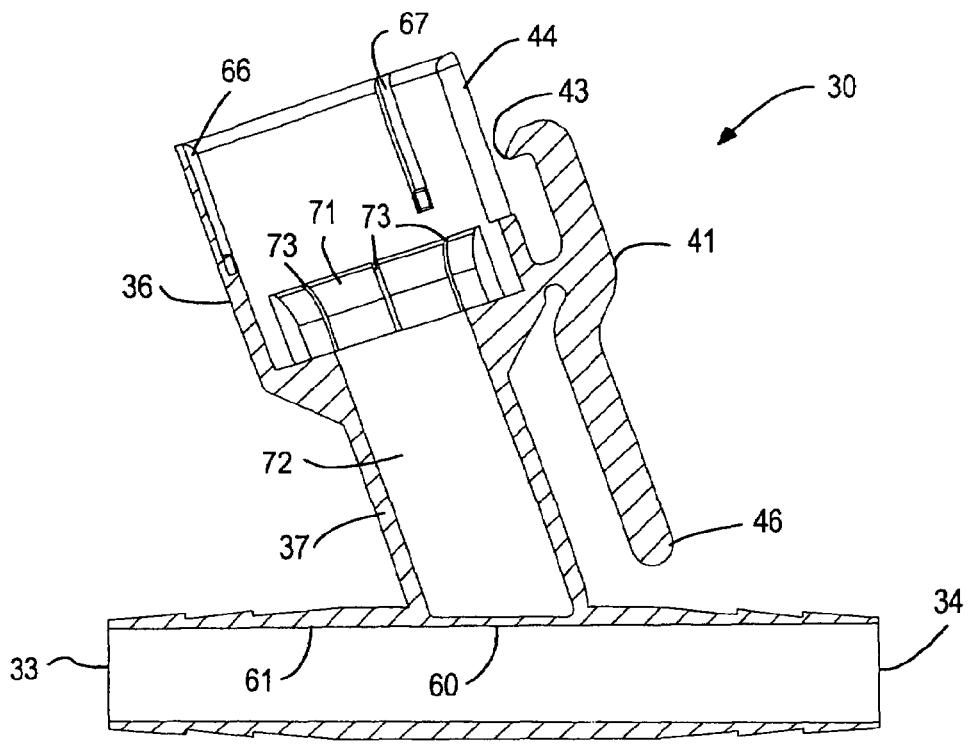
FIG. 8 is a vertical cross-section of the body member.

FIG. 8 shows a cross-section of body member 30 revealing a collar 71 at the lower end of upper transducer mounting section 36 which closely mates with transducer element 50 in order to accurately locate the transducer. Chamber 72 in lower sound coupling section 37 receives acoustic dampening material and then ultrasonic coupling gel which should completely fill the space within chamber 72 without air bubbles in order to provide the best ultrasonic performance. Therefore, it is preferable to overfill chamber 72 with ultrasonic coupling gel and to allow excess amounts to flow through a plurality of relief passages 73 cut into collar 71. Thus, as transducer element 50 is seated inside collar 71, the excess coupling gel is removed without the introduction of air bubbles.

Figure 9:
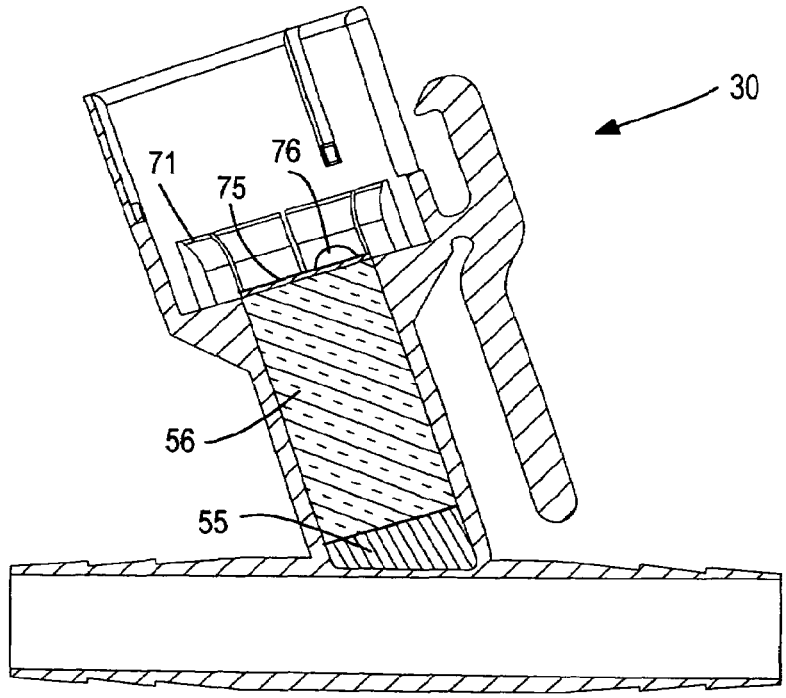
FIG. 9 is a vertical cross-section showing a pre-filled body member.

In another preferred embodiment as shown in FIG. 9, body member 30 may be pre-filled with acoustic coupling gel during manufacture, prior to distribution to the site of use. In that regard, a lid 75 may be provided within collar 71 so that coupling gel 56 is retained during transit. A pull tab 76 may be provided integral with lid 75 for easy removal of lid 75 at the time of use. In an alternative embodiment, lid 75 may be located at the top of collar 71 with ultrasonic coupling gel filling the space all the way up to lid 75.

By virtue of the construction of the emboli detection apparatus of the present invention, an especially convenient method can be employed to install the emboli detection system in a perfusion circuit in preparation for cardiac bypass surgery. The mounting connector (i.e., body member) is serially connected with the perfusion circuit tubing to receive blood flow at the desired location within the perfusion circuit using conventional tubing and methods. The space above the acoustic dampening material within the lower sound coupling section of the barrel piece is filled with ultrasonic coupling gel. Alternatively, if the unit was pre-filled with ultrasonic coupling gel, then the peel-off lid is removed. The ultrasonic transducer element is seated to the upper transducer mounting section in a keyed manner so that the circuit diameter can be automatically detected. As the transducer element is seated, excess ultrasonic coupling gel flows through the relief passages in the barrel piece to avoid air bubbles forming within the space between the ultrasonic transducer and the acoustic dampening material.

What is claimed is:

1. Emboli detection apparatus for coupling to circuit tubing of a perfusion circuit, comprising:
a body member including a substantially cylindrical flow passage having a containment wall extending between an inlet and an outlet, said body member including a barrel piece having a lower sound coupling section and an upper transducer mounting section, said barrel piece axially aligned with an acoustic window formed in said containment wall; and acoustic dampening material substantially filling a first space in said lower sound coupling section against said acoustic window;

wherein a second space is provided between said first space and said upper transducer mounting section for receiving ultrasonic coupling gel; and wherein said upper transducer mounting section includes a retainer for fixedly mounting an ultrasonic transducer adjacent said second space.

2. The apparatus of claim 1 wherein said body member is integrally molded and comprises a thermoplastic.

3. The apparatus of claim 1 wherein said acoustic window has a substantially flat upper surface in contact with an acoustic dampening material and a substantially cylindrically-shaped bottom surface formed by a portion of said containment wall.

4. The apparatus of claim 3 wherein said acoustic window has a minimum thickness greater than about 0.025 inches.

5. The apparatus of claim 3 wherein said acoustic window has minimum thickness in a range from about 0.025 inches to about 0.030 inches.

6. The apparatus of claim 1 further comprising:

an adapter for receiving a transducer element and having an external surface feature for mating with a keyed feature formed in said upper transducer mounting section.

7. The apparatus of claim 6 wherein said body member comprises a release lever having a catch for mating with a groove in an exterior surface of said adapter when said transducer element is fully seated.

8. The apparatus of claim 6 wherein said barrel piece includes relief passages for conducting excess coupling gel out of said barrel piece during seating of said transducer element.

9. The apparatus of claim 6 wherein said flow passage has a diameter selected from a plurality of predetermined diameters, wherein said body member provides a detectable property indicative of said selected diameter, and wherein said adapter includes a sensor for detecting said detectable property.

10. The apparatus of claim 9 wherein said detectable property comprises a magnetic field created by a magnet retained by said barrel piece at a position relative to said keyed feature, and wherein said adapter includes a plurality of magnetic sensors for providing respective detection signals to a controller that is further connected to said transducer element.

11. The apparatus of claim 1 wherein said flow passage has a diameter selected from a plurality of predetermined diameters, and wherein said body member provides a detectable property indicative of said selected diameter.

12. A mounting connector for receiving an ultrasonic transducer element of an emboli detection apparatus for coupling to circuit tubing of a perfusion circuit, comprising:

a body member including a substantially cylindrical flow passage having a containment wall extending between an inlet and an outlet, said body member including a barrel piece having a lower sound coupling section and an upper transducer mounting section, said barrel piece axially aligned with an acoustic window formed in said containment wall;

acoustic dampening material substantially filling a first space in said lower sound coupling section against said acoustic window;

an ultrasonic coupling gel substantially filling a second space between said first space and said upper transducer mounting section; and a peel-off lid mounted to an inside diameter of said barrel piece for sealing said coupling gel within said barrel piece.

13. The mounting connector of claim 12 wherein said ultrasonic coupling gel overfills said second space and impinges into said upper transducer mounting section, and wherein said peel-off lid is mounted substantially at the top of said ultrasonic coupling gel.

14. The mounting connector of claim 13 wherein said barrel piece includes relief passages for conducting excess coupling gel out of said upper transducer mounting section during seating of said ultrasonic transducer element.

15. A method of detecting emboli in blood flowing through circuit tubing of a perfusion circuit, said method comprising the steps of:

serially connecting a mounting connector with said circuit tubing, wherein said mounting connector comprises a body member including a substantially cylindrical flow passage having a containment wall extending between an inlet and an outlet, wherein said body member includes a barrel piece having a lower sound coupling section and an upper transducer mounting section, wherein said barrel piece is axially aligned with an acoustic window formed in said containment wall, and wherein an acoustic dampening material substantially fills a first space in said lower sound coupling section against said acoustic window;

filling a second space above said first space with an ultrasonic coupling gel;

seating an ultrasonic transducer element to said upper transducer mounting section; and flowing excess ultrasonic coupling gel through a relief passage in said barrel piece to avoid air bubbles forming in said second space.

16. The method of claim 15 wherein said ultrasonic coupling gel is pre-filled, and wherein said method further comprises the step of removing a peel-off lid over said ultrasonic coupling gel prior to seating said ultrasonic transducer element.

* * * * *